United States Patent [19]
Verrecchia

[11] Patent Number: 6,139,870
[45] Date of Patent: Oct. 31, 2000

[54] STABILIZED NANOPARTICLES WHICH ARE FILTERABLE UNDER STERILE CONDITIONS

[75] Inventor: Thierry Verrecchia, Arcueil, France

[73] Assignee: Aventis Pharma SA, Antony Cedex, France

[21] Appl. No.: 09/094,909

[22] Filed: Jun. 12, 1998

Related U.S. Application Data

[63] Continuation of application No. PCT/FR96/02015, Dec. 18, 1996.

[51] Int. Cl.[7] .............................. A61K 9/14; A61K 9/127
[52] U.S. Cl. ............................................. 424/450; 424/489
[58] Field of Search ..................... 424/489, 464, 424/490, 469, 470; 427/213

[56] References Cited

U.S. PATENT DOCUMENTS 5,118,528  6/1992  Fessi et al. ............................. 427/213

FOREIGN PATENT DOCUMENTS

WO 94/13654  6/1994  WIPO .

OTHER PUBLICATIONS

Allermann et al., Drug–Loaded Nanoparticles—Preparation Methods and Drug Targeting Issues, Eur. J. Pharm. Biopharm. 39 (5) pp. 173–191 (1993).

*Primary Examiner*—Thurman R. Page
*Assistant Examiner*—William E. Benston
*Attorney, Agent, or Firm*—Christine M. Hansen; Irving Newman; Ross Oehler

[57] ABSTRACT

Stabilized nanoparticles capable of being filtered under sterile conditions and including at least one hydrophobic, water-insoluble and non-water-dispersible polymer or copolymer (and optionally an active principle) emulsified in a solution of phospholipids and an oleic acid salt.

21 Claims, No Drawings

STABILIZED NANOPARTICLES WHICH ARE FILTERABLE UNDER STERILE CONDITIONS

This is a continuation application of International Application No. PCT/FR96/02015, filed on Dec. 18, 1996, published as WO 97/22337.

The present invention relates to very small-sized nanoparticles which display, besides the advantage of being able to circulate in the blood stream with no size problems in the capillaries, advantages of being stabilized, of being filterable under sterile conditions and of being lyophilizable.

Patent applications EP 523,183, EP 520,888 and EP 520,889 have described small-sized spherical particles which have the advantage of being injectable. However, the nanoparticles thus prepared have average diameters of about from 50 to 500 nm and would not be sterilizable by sterilizing filtration without a considerable loss in yield, and/or would not be lyophilizable owing to insufficient stability.

In Eur. J. Pharm. Biopharm., 39(5), 173–191 (1993) the authors examined the technologies currently available in the field of nanoparticles for use in the pharmaceutical industry. It is mentioned on page 182 that the sterile filtration of nanoparticle suspensions has never been described.

It has now been found, and this forms the subject of the present invention, that particles can be prepared, 95% of which have an average diameter of less than 100 nm, and more specifically have an average diameter of between 20 and 75 nm, and which can thus be subjected to a sterile filtration on 0.22 $\mu$m filters without a loss in yield. These particles are moreover more stable than those which could be obtained according to the prior art and can be lyophilized without leading to any phenomenon of particle agglomeration.

According to the invention, the nanoparticles comprise at least one hydrophobic, water-insoluble and water-indispersible polymer or copolymer emulsified in a solution or aqueous dispersion of phospholipids and of an oleic acid salt, in particular sodium oleate.

According to the invention, an active principle may be introduced with the polymer or the copolymer into the nanoparticles.

The phospholipids are chosen, by way of example, from natural, synthetic or semi-synthetic phospholipids; lecithins (phosphatidylcholine) such as, for example, purified egg or soya lecithins (lecithin E100®, lecithin E80® and phospholipons®, for example phospholipon 90®), phosphatidylethanolamine, phosphatidylserine, phosphatidylinositol, phosphatidylglycerol, dipalmitoylphosphatidylcholine, dipalmitoylglycerophosphatidylcholine, dimyristoylphosphatidylcholine, distearoylphosphatidylcholine and phosphatidic acid or mixtures thereof are used more particularly.

The hydrophobic, water-insoluble and water-indispersible polymer or copolymer may be chosen from biocompatible and biodegradable polymers, for example lactic or glycolic acid polymers and copolymers thereof, or polylactic/polyethylene (or polypropylene) oxide copolymers, preferably with molecular weights of between 1000 and 200000, polyhydroxybutyric acid polymers, polylactones of fatty acids containing at least 12 carbon atoms, or polyanhydrides.

The nanoparticles according to the invention are entirely suitable for use with hydrophobic active principles. The active principles which can be used may be chosen from the major classes of medicaments for use in human or veterinary medicine. They may also be chosen from principles for use in the cosmetics or agrifood industry or from diagnostic agents.

By way of example, active principles which are of interest in the pharmaceutical industry may be chosen, in a non-limiting manner, from antirheumatic, non-steroidal antiinflammatory, analgesic, antitussive and psychotropic agents, steroids, barbiturates, antimicrobial, antiallergenic, antiasthmatic, antispasmodic, antisecretory and cardiovascular agents, cerebral vasodilators, cerebral and hepatic protective agents, therapeutic agents of the gastrointestinal tract, anticancer or antiviral agents, vitamins, contraceptives, vaccines, etc.

According to the invention, the nanoparticles may be obtained by the technique of evaporation of solvent, from an aqueous dispersion or solution of phospholipids and of an oleic acid salt into which is added an immiscible organic phase comprising the active principle and the hydrophobic, water-insoluble and water-indispersible polymer or copolymer. The mixture is pre-emulsified and then subjected to homogenization and evaporation of the organic solvent to obtain an aqueous suspension of very small-sized nanoparticles.

The implementation of this process is described in greater detail in the examples.

The immiscible organic phase is preferably chosen from volatile solvents which can be good solvents for the polymer system chosen. For example, esters will be chosen such as, in particular, ethyl acetate, chlorinated solvents, for example dichloromethane or chloroform, or alternatively ketones such as methyl ethyl ketone.

In general, the active principle preferably constitutes about 25% by weight relative to the amount of polymer introduced. However, this amount may vary, and may optionally be lower or even range up to 50% by weight relative to the amount of polymer or copolymer introduced.

The immiscible organic phase is constituted such that the active principle and the polymer or the copolymer represent from 0.1 to 7% of the weight of the solution.

The aqueous phase consisting of an aqueous solution or dispersion of phospholipids and of oleic acid salt advantageously comprises these constituents in a respective molar proportion of 1/1. However, this proportion may vary such that the molar ratio of phospholipids relative to the oleic acid salt is from 0.1 to 1.

The aqueous phase is constituted such that the phospholipids and the oleic acid salt represent in total from 0.1 to 2% by weight in the solution.

The relative amounts of organic phase and of aqueous phase are chosen such that the organic phase represents 20 to 60% by volume relative to the aqueous phase.

The nanoparticles thus obtained may be filtered without giving rise to problems of caking together and in good yields. The filtration is carried out by cascade filtrations on filters of decreasing porosity, followed by a final filtration on a 0.22 $\mu$m filter.

Preferably, after filtration, the suspension obtained is lyophilized in the presence of one or more cryoprotective agents. The cryoprotective agent constitutes 5 to 20% (weight/volume) of the suspension subjected to lyophilization.

The solution for use in the lyophilization comprises certain additives such as nonionic compounds, for example a cryprotective agent or an agent to be used to adjust the isotonicity of the final solution to be injected. These agents may be chosen from sugars (glucose, mannitol, sorbitol or sucrose, for example), polymers [for example dextran (dextran 1500 or dextran 40000) polyvinylpyrrolidones which are injectable, polyethylene glycol, etc.], amino acids (for example glycine), or any other agent which can exercise this function. The solution may also contain one (or more) preserving agent(s). Where appropriate, the lyophilizate may be taken up, at the time of use, in water for injectable preparations. It is understood that such operations do not change the size of the particles.

The nanoparticles according to the invention are particularly advantageous on account of their stability. This stability makes it possible, in particular, to obtain a lyophilizate of good quality whose redissolution and/or resuspension, during use, is improved and for which the reconstituted suspension contains particles similar in diameter to that of the initial nanoparticles.

The nanoparticles according to the invention may be used for the preparation of sterile compositions for use in the pharmaceutical or veterinary fields, in the cosmetics or agrifoods field or for use in diagnostic agents.

This technique is particularly advantageous since it opens the way to the industrial-scale preparation of stabilized and decontaminated nanoparticle suspensions possibly charged with active principles, such a preparation not having been possible hitherto.

In addition, the stabilized nanoparticles according to the invention have a considerable advantage in the case of certain active principles such as, for example, anticancer agents of the taxoid family. The reason for this is that they make it possible to increase the activity of the product when compared with conventional formulations such as, in particular, formulations based on a polysorbate/ethanol mixture.

The present invention also relates to pharmaceutical compositions consisting of nanoparticles according to the invention, optionally in combination with one or more compatible and pharmaceutically acceptable excipients or adjuvants.

These compositions are preferably injectable compositions.

Parenteral administration comprises intravenous, intraperitoneal, intramuscular or subcutaneous administrations. Intraperitoneal or intravenous administration is more particularly preferred.

The compositions may contain at least 0.01% of therapeutically active product. The amount of active product in a composition is such that a suitable dosage can be prescribed. Preferably, the compositions are prepared such that a unit dose contains approximately from 0.01 to 1000 mg of active product for parenteral administration.

In man, the doses are generally between 0.01 and 200 mg/kg. Via the intravenous route, the doses are generally between 0.1 and 50 mg/kg, preferably between 0.1 and 8 mg/kg. It is understood that in order to select the dosage which is most appropriate, the route of administration, the weight of the patient, his general state of health, his age and all the factors which may influence the efficacy of the treatment will have to be taken into account.

The examples which follow, given without any limitation being implied, illustrate the present invention.

EXAMPLE 1

300 mg (15 mg/ml theoretical) of a diblock copolymer consisting of the combination of a poly(d,1-lactic acid) of mass 30 kD and of a polyethylene glycol of mass 2 kD (PLA-PEG) are dissolved in 8 ml of ethyl acetate (solution A). 70 mg of lecithin E80 and 50 mg of sodium oleate are dispersed in 20 ml of 5% w/v glucose solution (solution B). Solution A is emulsified in solution B with an Ultra-turrax stirrer and the pre-emulsion is then introduced into a Microfluidizer 110 S® type homogenizer for 3 minutes at 10° C. The volume of emulsion recovered is about 30 ml (30 g). The ethyl acetate is removed using a rotary evaporator at reduced pressure (100 mm of mercury) to a suspension volume of about 17 ml (17 g). The suspension is filtered through two filters in series, of decreasing porosity (1.2 $\mu$m Minisart NML®+0.22 $\mu$m SLGS®).

The average particle diameter measured by light scattering on a Brookhaven® machine is about 44 nm.

The optical density at 405 nm of the suspension before and after the final filtration through the 0.22 $\mu$m filter is 0.44.

EXAMPLE 2

A solution A is prepared in a similar manner to that of Example 1. 70 mg of lecithin E80 and 35 mg of sodium oleate are dispersed in 20 ml of 5% w/v glucose solution (solution B). Solution A is emulsified in solution B with an Ultra-turrax stirrer and the pre-emulsion is then introduced into a Microfluidizer 110 S® type homogenizer for 3 minutes at 10° C. The volume of emulsion recovered is about 30 ml (30 g). The ethyl acetate is removed using a rotary evaporator at reduced pressure (100 mm of mercury) to a suspension volume of about 17 ml (17 g). The suspension is filtered through two filters in series, of decreasing porosity (1.2 $\mu$m Minisart NML®+0.22 $\mu$m SLGS®).

The average particle diameter measured by light scattering on a Brookhaven® machine is about 46 nm.

The optical density at 405 nm of the suspension before and after the final filtration through the 0.22 $\mu$m filter is 0.64.

EXAMPLE 3

A solution A is prepared in a similar manner to that of Example 1. 70 mg of lecithin E80 and 20 mg of sodium oleate are dispersed in 20 ml of 5% w/v glucose solution (solution B). Solution A is emulsified in solution B with an Ultra-turrax stirrer and the pre-emulsion is then introduced into a Microfluidizer 110 S® type homogenizer for 3 minutes at 10° C. The volume of emulsion recovered is about 30 ml (30 g). The ethyl acetate is removed using a rotary evaporator at reduced pressure (100 mm of mercury) to a suspension volume of about 17 ml (17 g). The suspension is filtered through two filters in series, of decreasing porosity (1.2 $\mu$m Minisart NML®+0.22 $\mu$m SLGS®).

The average particle diameter measured by light scattering on a Brookhaven® machine is about 58 nm.

The optical density at 405 nm of the suspension before and after the final filtration through the 0.22 $\mu$m filter is 1.20.

EXAMPLE 4

A solution A is prepared in a similar manner to that of Example 1. 70 mg of lecithin E80 and 20 mg of sodium oleate are dispersed in 20 ml of 10% w/v glucose solution (solution B). Solution A is emulsified in solution B with an Ultra-turrax stirrer and the pre-emulsion is then introduced into a Microfluidizer 110 S® type homogenizer for 3 minutes at 10° C. The volume of emulsion recovered is about 30 ml (30 g). The ethyl acetate is removed using a rotary evaporator at reduced pressure (100 mm of mercury) to a suspension volume of about 17 ml (17 g). The suspension is filtered through two filters in series, of decreasing porosity (1.2 $\mu$m Minisart NML®+0.22 $\mu$m SLGS®)

The average particle diameter measured by light scattering on a Brookhaven® machine is about 61 nm.

The optical density at 405 nm of the suspension before and after the final filtration through the 0.22 μm filter is 0.90.

EXAMPLE 5

A solution A is prepared in a similar manner to that of Example 1. 70 mg of lecithin E80 and 20 mg of sodium oleate are dispersed in 20 ml of a 5% w/v maltose solution (solution B). Solution A is emulsified in solution B with an Ultra-turrax stirrer and the pre-emulsion is then introduced into a Microfluidizer 110 S® type homogenizer for 3 minutes at 10° C. The volume of emulsion recovered is about 30 ml (30 g). The ethyl acetate is removed using a rotary evaporator at reduced pressure (100 mm of mercury) to a suspension volume of about 17 ml (17 g). The suspension is filtered through two filters in series, of decreasing porosity (1.2 μm Minisart NML®+0.22 μm SLGS®).

The average particle diameter measured by light scattering on a Brookhaven® machine is about 57 nm.

The optical density at 405 nm of the suspension before and after the final filtration through the 0.22 μm filter is 1.10.

EXAMPLE 6

750 mg (15 mg/ml theoretical) of a diblock copolymer consisting of the combination of a poly(d,1-lactic acid) of mass 30 kD and of a polyethylene glycol of mass 2 kD (PLA-PEG) and 250 mg (5 mg/ml theoretical) of 4α,10β-diacetoxy-2α-benzoyloxy-5β,20-epoxy-1β-hydroxy-7β,8β-methylene-9-oxo-19-nor-11-taxen-13α-yl(2R,3S)-3-tert-butoxycarbonylamino-2-hydroxy-3-phenyl propionate are dissolved in 20 ml of ethyl acetate (solution A). 175 mg of lecithin E80 and 90 mg of sodium oleate are dispersed in 50 ml of 5% w/v glucose solution (solution B). Solution A is emulsified in solution B with an Ultra-turrax stirrer and the pre-emulsion is then introduced into a Microfluidizer 110 S® type homogenizer for 10 minutes at 10° C. The volume of emulsion recovered is about 70 ml (70 g). The ethyl acetate is removed using a rotary evaporator at reduced pressure (100 mm of mercury) to a suspension volume of about 45 ml (45 g). The suspension is filtered through two filters in series, of decreasing porosity (1.2 μm Minisart NML®+0.22 μm SLGS®). The filtered suspension is sterile.

The average particle diameter measured by light scattering on a Brookhaven® machine is about 66 nm.

The optical density at 405 nm of the suspension before and after the final filtration through the 0.22 μm filter is 2.8.

The manufacturing yield, expressed by the ratio of the final 4α,10β-diacetoxy-2α-benzoyloxy-5β,20-epoxy-1β-hydroxy-7β,8β-methylene-9-oxo-19-nor-11-taxen-13α-yl(2R,3S)-3-tert-butoxycarbonylamino-2-hydroxy-3-phenylpropionate concentration after filtration to the initial theoretical concentration (5 mg/ml) is greater than 90%.

The concentration of PLA-PEG (calculated relative to the yield of 4α,10β-diacetoxy-2α-benzoyloxy-5β,20-epoxy-1β-hydroxy-7β,8β-methylene-9-oxo-19-nor-11-taxen-13α-yl(2R,3S)-3-tert-butoxycarbonylamino-2-hydroxy-3-phenylpropionate) is 14 mg/ml.

The suspension undergoes no chemical change (absence of degradation of the active material) or physical change (the particle size and the optical density remain identical) after storage for 4 months at 4° C. and 25° C.

The 4α,10β-diacetoxy-2α-benzoyloxy-5β,20-epoxy-1β-hydroxy-7β,8β-methylene-9-oxo-19-nor-11-taxen-13a-yl(2R,3S)-3-tert-butoxycarbonylamino-2-hydroxy-3-phenylpropionate may be prepared as described in patent application WO 94/13654.

EXAMPLE 7

750 mg (15 mg/ml theoretical) of a diblock copolymer consisting of the combination of a poly(d,1-lactic acid) of mass 30 kD and of a polyethylene glycol of mass 2 kD (PLA-PEG) are dissolved in 20 ml of ethyl acetate (solution A). 175 mg of lecithin E80 and 90 mg of sodium oleate are dispersed in 50 ml of 5% w/v glucose solution (solution B). Solution A is emulsified in solution B with an Ultra-turrax stirrer and the pre-emulsion is then introduced into a Microfluidizer 110 S® type homogenizer for 10 minutes at 10° C. The volume of emulsion recovered is about 70 ml (70 g). The ethyl acetate is removed using a rotary evaporator at reduced pressure (100 mm of mercury) to a suspension volume of about 45 ml (45 g). The suspension is filtered through two filters in series, of decreasing porosity (1.2 μm Minisart NML®+0.22 μm SLGS®). The filtered suspension is sterile.

The average particle diameter measured by light scattering on a Brookhaven® machine is about 63 nm.

The optical density at 405 nm of the suspension before and after the final filtration through the 0.22 μm filter is 1.6.

The suspension undergoes no physical change (the particle size and the optical density remain identical) after storage for 4 months at 4° C. and 25° C.

EXAMPLE 8

750 mg (15 mg/ml theoretical) of a diblock copolymer consisting of the combination of a poly(d,1-lactic acid) of mass 30 kD and of a polyethylene glycol of mass 2 kD (PLA-PEG) and 250 mg (5 mg/ml theoretical) of 4α,10β-diacetoxy-2α-benzoyloxy-5β,20-epoxy-1β-hydroxy-7β,8β-methylene-9-oxo-19-nor-11-taxen-13α-yl(2R,3S)-3-tert-butoxycarbonylamino-2-hydroxy-3-phenylpropionate are dissolved in 10 ml of ethyl acetate (solution A). 175 mg of lecithin E80 and 45 mg of sodium oleate are dispersed in 50 ml of 5% w/v glucose solution (solution B). Solution A is emulsified in solution B with an Ultra-turrax stirrer and the pre-emulsion is then introduced into a Microfluidizer 110 S® type homogenizer for 10 minutes at 10° C. The volume of emulsion recovered is about 60 ml (60 g). The ethyl acetate is removed using a rotary evaporator at reduced pressure (100 mm of mercury) to a suspension volume of about 36 ml (36 g). The suspension is filtered through two filters in series, of decreasing porosity (1.2 μm Minisart NML®+0.22 μm SLGS®). The filtered suspension is sterile.

The average particle diameter measured by light scattering on a Brookhaven® machine is about 64 nm.

The optical density at 405 nm of the suspension before and after the final filtration through the 0.22 μm filter is 1.5.

The manufacturing yield, expressed by the ratio of the final 4α,10β-diacetoxy-2α-benzoyloxy-5β,20-epoxy-1β-hydroxy-7β,8β-methylene-9-oxo-19-nor-11-taxen-13β-yl(2R,3S)-3-tert-butoxycarbonylamino-2-hydroxy-3-phenylpropionate concentration after filtration to the initial theoretical concentration (5 mg/ml) is greater than 90%.

The proportion of 4α,10β-diacetoxy-2α-benzoyloxy-5β,20-epoxy-1β-hydroxy-7β,8β-methylene-9-oxo-19-nor-11-taxen-13α-yl(2R,3S)-3-tert-butoxycarbonylamino-2-hydroxy-3-phenylpropionate encapsulated in the nanoparticles, measured by assaying the supernatent after ultracentrifugation (65000 G, 2 h), is about 98%.

The concentration of PLA-PEG (calculated relative to the yield of 4α,10β-diacetoxy-2α-benzoyloxy-5β,20-epoxy-1β-hydroxy-7β,8β-methylene-9-oxo-19-nor-11-taxen-13α-yl(2R,3S)-3-tert-butoxycarbonylamino-2-hydroxy-3-phenylpropionate) is 14 mg/ml.

The 4α,10β-diacetoxy-2α-benzoyloxy-5β,20-epoxy-1β-hydroxy-7β,8β-methylene-9-oxo-19-nor-11-taxen-13α-yl (2R,3S)-3-tert-butoxycarbonylamino-2-hydroxy-3-phenylpropionate may be prepared as described in patent application WO 94/13654.

EXAMPLE 9

3.0 g (15 mg/ml theoretical) of a diblock copolymer consisting of the combination of a poly(d,l-lactic acid) of mass 30 kD and of a polyethylene glycol of mass 2 kD (PLA-PEG) are dissolved in 80 ml of ethyl acetate (solution A). 700 mg of lecithin E80 and 180 mg of sodium oleate are dispersed in 200 ml of water for an injectable preparation (solution B). Solution A is emulsified in solution B with an Ultra-turrax stirrer and the pre-emulsion is then introduced into a Microfluidizer 110 S® type homogenizer for 10 minutes at 10° C. The volume of emulsion recovered is about 230 ml (230 g). The ethyl acetate is removed using a rotary evaporator at reduced pressure (100 mm of mercury) to a suspension volume of about 186 ml (186 g). The volume of the suspension is adjusted to a volume of 200 ml with water for an injectable preparation. The suspension is filtered through two filters in series, of decreasing porosity (1.2 μm Minisart NML®+0.22 μm SLGS®). The filtered, sterile suspension is lyophilized in the presence of 20% w/v sucrose.

The average particle diameter measured by light scattering on a Brookhaven® machine before lyophilization and after uptake of the lyophilizate with the same volume of water for an injectable preparation is between 70 and 100 nm.

What is claimed is:

1. A stable nanoparticle suspension comprising at least one hydrophobic, water-insoluble and water indispersible polymer or copolymer emulsified in an aqueous phase comprising a phospholipid and an oleic acid salt.

2. The suspension of claim 1, which is filterable under sterile conditions.

3. The suspension of claim 1, which is filtered by sterile filtration.

4. The suspension of claim 3 which further comprises an active principle.

5. The suspension of claim 4, wherein the oleic acid salt is sodium oleate.

6. The suspension of claim 4, wherein the average diameter of about 95% of the particles is less than 100 nm.

7. The suspension of claim 4, wherein the copolymer consists essentially of the combination of poly (d,l-lactic acid) and polyethylene glycol.

8. A process for the preparation of nanoparticles which comprises:

(a) preparing an aqueous dispersion or solution of at least one phospholipid and at least one oleic acid salt;

(b) adding thereto an organic phase comprising a hydrophobic, water-insoluble and water-indispersible polymer or copolymer and an organic solvent;

(c) homogenizing the resulting mixture;

(d) removing the organic solvent; and (e) filtering the resulting suspension.

9. The process of claim 8, wherein an active principle is added to the organic phase before homogenization of the aqueous and organic phases.

10. The process of claim 9, wherein the filtration is sterilizing filtration.

11. The process of claim 10, further comprising lyophilizing the resulting suspension.

12. The process of claim 10, wherein the oleic acid salt is sodium oleate.

13. The process of claim 10, herein the copolymer consists essentially of the combination of poly(d,l-lactic acid) and polyethylene glycol.

14. The process of claim 10, wherein the sterilizing filtration is carried out by sequential use of filters of decreasing porosity.

15. A nanoparticle produced in accordance with the process of claim 9.

16. A nanoparticle produced in accordance with the process of claim 11.

17. A nanoparticle produced in accordance with the process of claim 12.

18. A pharmaceutical composition comprising nanoparticles produced in accordance with the process of claim 9.

19. The pharmaceutical composition of claim 18, wherein the active principle is an anticancer agent of the taxoid family.

20. The pharmaceutical composition of claim 19, wherein the composition is injectable.

21. The suspension of claim 6 wherein said average diameter is between 20 and 70 nm.

* * * * *